United States Patent [19]

Kieffer, III et al.

[11] 4,380,998

[45] Apr. 26, 1983

[54] SOFT TIP SPECULUM

[75] Inventors: Joseph D. Kieffer, III, Camillus; John Cecil, Jr.; Barden A. Conroe, both of Skaneateles, all of N.Y.

[73] Assignee: Welch Allyn, Inc., Skaneateles Falls, N.Y.

[21] Appl. No.: 222,281

[22] Filed: Jan. 5, 1981

[51] Int. Cl.³ .............................................. A61B 1/22
[52] U.S. Cl. .................................. 128/9; 128/132 R; 128/151; 128/343
[58] Field of Search .............................. 128/9, 4–8, 128/343, 132 R, 746, 151

[56] References Cited

U.S. PATENT DOCUMENTS

| 2,797,684 | 8/1955 | Moore | 128/9 |
| 3,224,437 | 4/1962 | Hardgrove | 128/9 |
| 3,384,076 | 11/1966 | Speelman | 128/9 |
| 3,698,387 | 10/1972 | Moore et al. | 128/9 |
| 3,949,740 | 4/1976 | Twentier | 128/9 |

Primary Examiner—Lee S. Cohen
Assistant Examiner—Angela D. Sykes
Attorney, Agent, or Firm—Bruns & Jenney

[57] ABSTRACT

A removable speculum for use in conjunction with an otoscope. The speculum contains a soft, rubber-like tip bonded upon the distal end thereof for protecting the ear canal and forming a seal therewith. An internal seal is also provided that acts between the speculum and a receiving surface upon the otoscope.

7 Claims, 4 Drawing Figures

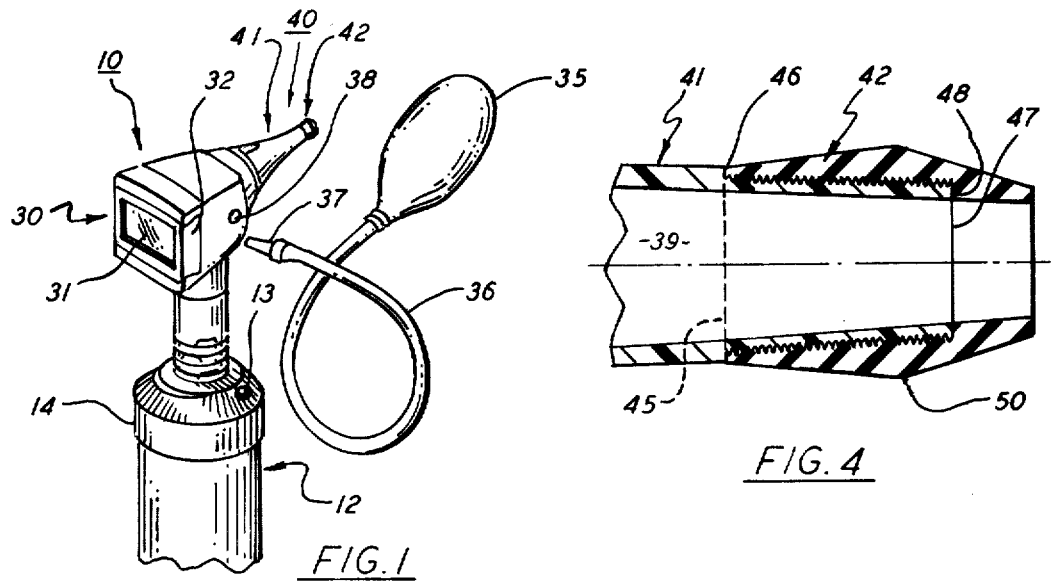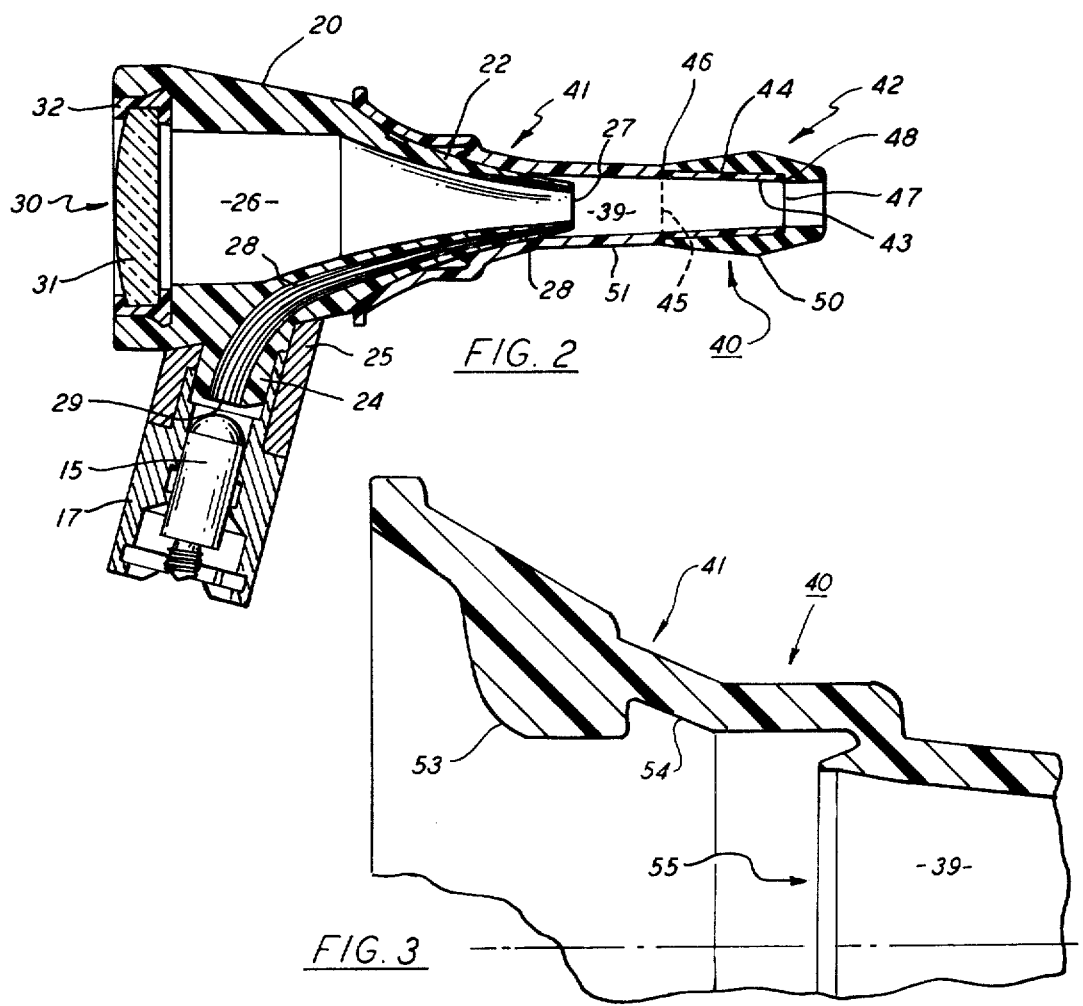

SOFT TIP SPECULUM

BACKGROUND OF THE INVENTION

This invention relates to an improved speculum for use in conjunction with an otoscope or the like that includes a soft, rubber-like tip at the distal end thereof that provides for the safety and comfort of the patient. The soft tip also forms a positive seal against the ear canal during insufflation thus allowing air under pressure to be introduced in the ear when a visual examination of the ear drum is being made.

Two types of otoscopes are used by physicians in examining and/or treating the ear. One is an operative instrument through which other smaller instruments are passed to gain access to various parts of the inner ear. The other is a diagnostic instrument which is used to visually observe the functional activity of the ear, particularly the vibratory response of the ear drum to air under pressure. In either case, it is typical to equip the instrument with a removable speculum that can be inserted into the ear canal to hold it in a dilated condition while the examination or treatment is being carried out. Usually specula come in different sizes and can be interchangeably used with either an operative or a diagnostic instrument.

Heretofore, removable specula were formed from a single piece of material. In the more conventional design, the speculum takes the form of a conical, hollow structure that is necked down at the distal end to allow for ease of entry into the ear canal. The speculum typically is formed of a rigid material that will not deform or flex when it is brought into contact with another body and, as a consequence, there always exists a danger that the speculum might harm the delicate ear parts. Any slight hand pressure upon the body of the instrument is magnified into a relatively high force at the tip of the speculum. This is particularly true where the instrument must be maneuvered within the ear canal to more accurately focus the distal end of the instrument upon the region of interest.

It should be further noted that single piece specula found in the prior art, which are made of hard materials, do not necessarily conform to the shape of the ear canal. Accordingly, air, which is sometimes introduced into the canal under pressure during the course of certain examinations, will escape around the specula and thus render the results of the examination less than satisfactory.

SUMMARY OF THE INVENTION

It is therefore an object of the present invention to provide an improved apparatus for examining the ear.

It is a further object of the present invention to provide for the comfort and safety of a patient undergoing an ear examination.

A still further object of the present invention is to provide a removable speculum for use in conjunction with an otoscope that has a soft tip and a rigid body.

Another object of the present invention is to provide a speculum having a tip that is capable of conforming to the contour of the ear canal and thus provide a good pneumatic seal against the wall of the canal.

Yet another object of the present invention is to provide a removable speculum having an internal seal that acts between the speculum and a receiving surface on an associated otoscope.

While a still further object of the present invention is to provide a removable speculum that is capable of sealing against both the inner wall of the ear canal and the associated otoscope during insufflation of the ear.

These and other objects of the present invention are attained by means of a removable speculum for use in conjunction with an otoscope having a hard body and a soft rubber-like tip secured to the distal end thereof that is capable of protecting the ear canal and also forming a conforming seal therewith during insufflation of the ear. A seal is also provided between the speculum and the mating surface of the otoscope to further prevent air from leaking from the system.

BRIEF DESCRIPTION OF THE DRAWINGS

For a better understanding of these and other objects of the present invention reference is had to the following detailed description of the invention which is to be read in conjunction with the associated drawings, wherein:

FIG. 1 is a perspective view of an otoscope mounted on the upper part of a supporting battery handle, the otoscope having a removable speculum embodying the present invention mounted thereon;

FIG. 2 is an enlarged vertical section through the otoscope illustrated in FIG. 1 with the removable speculum mounted thereon;

FIG. 3 is also an enlarged, partial sectional view of a speculum embodying the teachings of the present invention showing the construction of an internal sealing ring utilized therein; and FIG. 4 is a further enlrged, partial sectional view of a speculum embodying the teachings of the present invention showing one method of bonding the tip thereof to the body of the speculum.

DETAILED DESCRIPTION OF THE INVENTION

With specific reference to the drawings, an otoscope, generally referenced 10, is shown mounted upon a battery handle 12 of the type disclosed in U.S. Pat. No. 3,071,747. The battery handle is of a size and shape such that it can be easily grasped by a physician or a trained person conducting an examination. The instrument contains batteries (not shown), a switch button 13 and a rheostat dial 14. The batteries provide energy to a lamp 15 (FIG. 2) mounted in a metal sleeve 17 which forms part of the otoscope base.

The otoscope is basically comprised of a head portion 20 and a specular extension 22 which preferably has a one piece construction. The head portion has a substantially rectangular configuration in rear elevation and its three dimensional shape is that of a trapezoidal polyhedron as best shown in FIG. 1. The specular extension has a substantially frustoconical configuration although its wall elements have a slightly concave curvature as indicated in FIG. 2. The head piece includes a cylindrical lug 24 which is cemented to a tubular throat piece 25 and the base sleeve 17 of the instrument.

The otoscope is formed with an unobstructed passage 26 which extends continually through the head and specular extension. The passage is of sufficient size to permit ease of viewing or to permit a smaller instrument to be passed therethrough. The passage is encircled at its distal end 27 by a pre-formed fiber optic bundle 28 that is embedded in the passage wall and which serves to transmit light from the lamp and direct it outwardly from the distal end of the specular extension. The bundle becomes cylindrical as it approaches the lamp and terminates in a polished entrance face 29 adjacent to the lamp. Light received from the lamp is thus distributed in an annular pattern at the distal end of the instrument to illuminate the field of view.

A slide 30 comprised of a suitable lens 31 and a frame 32 is slidably received within the rear of the instrument head. The frame is formed of an elastomer material that is capable of forming a seal against the contacting surface of the head. With the slide in place the otoscope can be used as a diagnostic instrument and with it removed it can be used as an operative instrument. An inflation bulb 35 and a flexible connecting tube 36 having an end fitting 37 can be connected into a receiving port 38 contained in the head of the instrument. Through use of the bulb the examining physician can gently insufflate the ear canal which causes the ear drum to vibrate and thus provides a visual indication of its condition.

The otoscope is equipped with a removable, hollow speculum, generally referenced 40. The speculum opening 39 forms an extension of the access opening 26 and serves to protect the fiber ends and to channel light emitted from the bundle into the area under examination. The speculum assembly contains a frusto-conical body section 41 formed of a relatively hard material such as polypropylene or the like and a relatively soft tip 42 formed of a suitable rubber-like material. The soft tip is a hollow, cylindrical element that is mounted upon the distal end of the speculum body and is securely bonded thereto to prevent the tip from separating from the body when the instrument is used under actual working conditions. In assembly, the distal end of the speculum body is provided with a reduced diameter extension 43. The extension is fitted into an expanded blind hole 44 that is coaxially aligned with the main opening passing through the tip. The blind hole is passed inwardly from the rear end face 45 of the tip to a depth that is substantially equal to the axial length of the reduced diameter extension. As a result of this construction, the rear end face of the tip is seated in abutting contact against the radial shoulder 46 on the speculum body while the terminal end face 47 of the extension is similarly seated against the flat bottom surface 48 of the blind hole.

The soft tip is preferably joined to the reduced diameter extension by thermally bonding the two members together along their commonly shared boundaries. The materials making up the tip and the speculum body are formed from similar base materials that reach a semi-molten state at about the same elevated temperature. Upon cooling, the materials coalesce to form an extremely strong and permanent bond along the line of contact. Alternatively, the tip may be secured to the speculum body either using a high strength adhesive or providing for a strictly mechanical bond. As best seen in FIG. 4, one method of forming a mechanical bond is to provide an interference fit between the blind hole formed in the soft tip and the outer surface of the reduced diameter extension. The outer surface of the extension is roughened to establish a series of sharp peaks. The tip is press-fitted over the roughened extension whereupon the soft tip material is compacted or otherwise forced into the valleys between the peaks thereby enhancing the mechanical bond between the parts. The axial length of the extension is about equal to 0.75 the length of the tip whereby the raised diameter section of the tip overlies the extension and is thus prevented from collapsing into the access opening as the speculum is manipulated in the ear canal.

The soft tip is configured so that its diameter at about its midregion is greater than the diameter at the front face and the rear face. As best seen in FIG. 2, the outside wall of the tip slopes inwardly from the region of maximum diameter toward each end face. The diameter of the rear end face of the tip, that is, the end face that abuts the shoulder 46 of the reduced diameter extension 43, is equal to the outside diameter of the shoulder to provide a relatively smooth surface along the line of joinder. The larger diameter section of the tip forms a readily deformable sealing surface 50 that is capable of conforming to the geometry of the ear canal wall to establish a positive seal thereagainst. It should be noted that the sealing surface 50 also provides a fulcrum-like pivot about which the instrument may be safely and comfortably maneuvered within the ear canal without breaking the pneumatic seal.

The internal opening formed in the speculum body is expanded at the proximal end thereof to provide a contoured inner wall 54 (FIG. 3) that compliments the contour of the mating specular extension 22 on the otoscope. A small locking lug 53 is carried upon the contoured wall which engages a slot in the specular extension of the otoscope to releasably secure the parts together in assembly. The locking arrangement is not considered novel per se and is disclosed in further detail in U.S. Pat. No. 3,146,775.

An annular sealing ring 55 is also contained within the contoured opening at the proximal end of the speculum. In practice, the ring depends inwardly from the contoured wall surface and is adapted to contact the mating surface of the otoscope and provide a tight seal therebetween. The annular sealing ring is fabricated of a resilient material that is easily deformed into conformity with the mating otoscope surface when the parts are locked in place in assembly. Preferably, the seal is formed as an integral part of the speculum body that is formed as part of the overall structure when the speculum is fabricated. Typically, the speculum body is cast or molded from a plastic material that is ideally well suited for use as a seal in which case the seal and speculum body can be formed from a single piece of material as shown in FIG. 3.

From the foregoing description of the preferred embodiment of the invention, it will be apparent that a speculum construction has been disclosed which provides substantial improvement over the prior art, the construction being at the same time economical to produce and efficient in operation.

We claim:

1. A removable speculum for use in conjunction with an instrument that is inserted into the ear canal and includes a general frusto-conical body formed of a rigid material having an extended section disposed outwardly from the smaller end wall of the body and having a reduced diameter with respect to the smaller end wall, so as to form a radially extended shoulder therewith, the extended section terminating in a front end face, said body and said reduced diameter extended section having an unobstructed access opening passing therethrough, a locking means for removably securing the body to the instrument, a hollow cylindrical tip mounted upon said extended section that is formed of a soft flexible material that conforms against the wall of the ear canal to establish a positive seal thereagainst, said tip having a rear wall that is seated against said shoulder and a front wall that passes over and abuts against the front end face of the extended section, whereby the tip is prevented from moving axially on the extended section and collapsing into said opening as it is inserted and maneuvered in the ear canal, and said tip further having a raised midsection that overlies the extended section and tapers downwardly toward each wall whereby the tip can be maneuvered in the ear without breaking the seal.

2. The speculum of claim 1 wherein the outer periphery of the shoulder complements the outer periphery of the rear wall of said tip to provide a smooth surface at the point where the tip is seated against the body.

3. The speculum of claim 2 that further includes a rearwardly disposed resilient circular lip connected to the inner wall of the access opening that is capable of being placed in sealing contact against the instrument for providing a seal thereagainst.

4. The speculum of claim 1 wherein said tip is formed of a material that is thermally bonded to the body.

5. The speculum of claim 1 wherein the outer surface of the extended section is roughened to provide a mechanical bond against the inside surface of the hollow tip.

6. The speculum of claim 1 wherein the axial length of the extended section is approximately 0.75 that of the length of the tip.

7. A speculum for use in conjunction with an instrument that is insertable into the ear canal that includes
- a rigid support body having first and second ends and an extended section protruding from the second end thereof and terminating in an end face for receiving a soft tip thereupon, said support body and extended section having a hole passing therethrough,
- a locking means for removably securing the body to the instrument,
- a soft tip of generally cylindrical form mounted upon the extended section of said body, said tip being formed of a soft resilient material that readily conforms to the contour of the ear canal to create a seal thereagainst,
- said soft tip being hollow and having an internal shoulder formed therein that seats against the end face of the extended section to prevent the tip from moving axially as it is passed into the ear canal,
- said soft tip further including a raised midsection that overlies the extended section of the body and which tapers down toward each end of the tip so that the raised section contacts the ear canal to form said conforming seal without collapsing into the hole passing through said extension.

* * * * *